United States Patent
Hicks et al.

(10) Patent No.: US 10,478,460 B2
(45) Date of Patent: Nov. 19, 2019

(54) METHOD FOR IDENTIFYING A MAMMAL RECEPTIVE TO EMBRYO TRANSFER

(75) Inventors: Brady Hicks, Boise, ID (US); Donna S. Clark, Boise, ID (US)

(73) Assignee: J.R. Simplot Company, Boise, ID (US)

(*) Notice: Subject to any disclaimer, the term of this patent is extended or adjusted under 35 U.S.C. 154(b) by 0 days.

(21) Appl. No.: 13/495,656

(22) Filed: Jun. 13, 2012

(65) Prior Publication Data
US 2013/0006047 A1    Jan. 3, 2013

Related U.S. Application Data

(60) Provisional application No. 61/496,761, filed on Jun. 14, 2011.

(51) Int. Cl.
A61B 17/435 (2006.01)
G01N 33/566 (2006.01)
A61K 35/54 (2015.01)

(52) U.S. Cl.
CPC .................................. *A61K 35/54* (2013.01)

(58) Field of Classification Search
CPC ................ A61K 35/54; A01K 2207/12; A01K 67/0275; G01N 33/53; A61D 19/04; A61B 17/435
USPC ............ 600/33–35, 551; 514/9.9, 10.1, 800; 436/501; 435/325; 800/8; 437/7.92, 18; 604/906
See application file for complete search history.

(56) References Cited

U.S. PATENT DOCUMENTS

| 4,780,451 A | 10/1988 | Donaldson |
| 7,083,575 B1 | 8/2006 | Claycomb et al. |
| 2007/0042449 A1 | 2/2007 | Hivorel et al. |
| 2008/0300450 A1 | 12/2008 | Schrick |
| 2010/0312137 A1 | 12/2010 | Gilmour et al. |

FOREIGN PATENT DOCUMENTS

NZ    619785    8/2016

OTHER PUBLICATIONS

Efficacy of timed embryo transfer with fresh and frozen in vitro produced embryos to increase pregnancy rates in heat-stressed dairy cattle. Ambrose JD, Drost M, Monson RL, Rutledge JJ, Leibfried-Rutledge ML, Thatcher MJ, Kassa T, Binelli M, Hansen PJ, Chenoweth PJ, Thatcher WW. J Dairy Sci. Nov. 1999; 82(11):2369-76.*

M. A. Kakar, G. Rasool and F. Ahmad. Clinical incidence of reproductive disorders in crossbred cows in the province of Balochistan. Pakistan Vet. J., 17 (1): 1997: pp. 9-12.*

(Continued)

*Primary Examiner* — Navin Natnithithadha
*Assistant Examiner* — Sunita Reddy
(74) *Attorney, Agent, or Firm* — Cooley LLP (57) ABSTRACT

The present invention is drawn to novel methods of selecting mammals receptive to embryo transfers in order to improve reproductive efficiency and milk production of the mammals. The present invention encompasses three methods: (1) selecting from any group of mammals; (2) selecting from estrus-negative mammals; and (3) selecting from estrus-negative mammals and pooling the selected mammals with estrus-positive mammals. Also encompassed is a kit for selecting mammals receptive to embryo transfers.

24 Claims, 5 Drawing Sheets

(56) References Cited

OTHER PUBLICATIONS

Detection of a corpus luteum in apparently anoestrous cows by manual palpation, transrectal ultrasonography and plasma progesterone concentration, S. McDougall & F.M. Rhodes, pp. 47-52, New Zealand Veterinary Journal vol. 47 , Iss. 2, 1999.(attached).*
Reproductive culling: who, when, and why. Dairy Pipeline: Mar. 1996, by Ray L. Nebel, Extension Dairy Scientist, Reproduction, Virginia Tech, Virginia Cooperative Extension, Virginia Tech, Virginia State University.(attached).*
Baker et al., "Commercial Splitting of Bovine Embryos", *Theriogenology*, Jan. 1985, pp. 3-12, vol. 23, No. 1.
Gray et al., "The Commercial Application of Embryo Splitting in Beef Cattle", *Theriogenology*, Jan. 1991, pp. 37-44, vol. 35, No. 1.
Heuwieser et al., "Fertilization of Bovine Oocytes after Microsurgical Injection of Spermatozoa", *Theriogenology*, (1992), pp. 1-9, vol. 38, Butterworth-Heinemann.
Bodo et al., "Preimplantation Genetic Diagnosis in Cattle: A Review", *Acta Veterinaria Hungarica*, (2001), pp. 99-109, Akademiai Kiado, Budapest.
Lamb et al., "Effectiveness of Select Synch (Gonadotropin-Releasing Hormone and Prostaglandin $F_{2\alpha}$) for Synchronizing Estrus in Replacement Beef Heifers", *The Professional Animal Scientist*, (2004), pp. 27-33, vol. 20.
Duponte et al., "Three Simplified Estrus Synchronization Programs for Hawaii's Beef Breeding Season", *Livestock Management*, Apr. 2007, pp. 1-2, LM-14, Cooperative Extension Service, University of Hawaii at Manoa.
Chen et al., "Efficient Production of Transgenic Cloned Calves Using Preimplantation Screening", *Biology of Reproduction*, (2002), pp. 1488-1492, Society for the Study of Reproduction, Inc.
Lai et al., "Creating Genetically Modified Pigs by Using Nuclear Transfer", *Reproductive Biology and Endocrinology*, (2003), pp. 1-6, vol. 1, http:www.rbej.com/content/1/1/82.
Clark, John, "Genetic Modification of Milk Proteins", *Am J Clin Nutr*, (1996), pp. 633S-638S, vol. 63, American Society for Clinical Nutrition.
Yang et al., "Characterization of Bioactive Recombinant Human Lysozyme Expressed in Milk of Cloned Transgenic Cattle", *Plos One*, Mar. 2011, pp. 1-10, vol. 6, Issue 3.
Smith et al., "Influence of Nuclear and Cytoplasmic Activity on te Development of Nivo of Sheep Embryos after Nuclear Transmplantation", *Biology of Reproduction*, (1989), pp. 1027-1035, vol. 40, University of Montreal, Saint-Hyacinthe, Quebec, Canada.
Peura et al., "The Effect of Recipient Oocyte Volume on Nuclear Transfer in Cattle", *Molecular Reproduction and Development*, (1998), pp. 185-191, vol. 50, Wiley-Liss, Inc.
Wilmut et al., "Viable Offspring Derived from Fetal and Adult Mammalian Cells", *Nature*, Feb. 27, 1997, pp. 810-813, vol. 385.
Kato et al., "Eight Calves Cloned from Somatic Cells of a Single Adult", *Science*, Dec. 11, 1998, pp. 2095-2098, vol. 282, www.sciencemag.org.
PCT International Search Report and Written Opinion of the International Searching Authority, International Application No. PCT/US2012/042212, dated Sep. 7, 2012, 7 pages.
Demetrio et al., "Factors Affecting Conception Rates Following Artificial Insemination or Embryo Transfer in Lactating Holstein Cows", *J. Dairy Sci.*, (2007), pp. 5073-5082, vol. 90, No. 11, American Dairy Science Association.
Bo et al., "The Control of Follicular Wave Development for Self-Appointed Embryo Transfer Programs in Cattle", *Theriogenology*, (2002), pp. 53-72, vol. 57, Elsevier Science Inc.
Alila et al., "Origin of Different Cell Types in the Bovine Corpus Luteum as Characterized by Specific Monoclonal Antibodies", *Biology of Reproduction*, (1984), pp. 1015-1025, vol. 31.
Office Action, Chinese Application Serial No. 201280034563.1, dated Feb. 25, 2015. (11 pages).
Chebel, Ricardo C., et al. "Factors affecting conception rate after artificial insemination and pregnancy loss in lactating dairy cows." *Animal Reproduction Science* (2004); 84.3: 239-255.
Mei Donglin, Studies on the Relative Technologies of Embryo Transfer in Cow, Full-text *Database of China Excellent Master's Thesis (Electronic Journal)*, Yanbian University, China, Date of Submission—Oct. 2005, Date of Defense—Jan. 2006, 10 pages, with English translation.

\* cited by examiner

METHOD FOR IDENTIFYING A MAMMAL RECEPTIVE TO EMBRYO TRANSFER

CROSS-REFERENCE TO RELATED APPLICATION

This application claims priority to U.S. provisional application No. 61/496,761, filed Jun. 14, 2011, the entire contents of which are incorporated herein by reference.

FIELD OF THE INVENTION

The present technology relates to the identification of reproductive mammals that, prior to the inventive technology, would have been classified as unreceptive to embryo transfer and artificial insemination methods for inducing pregnancy.

BACKGROUND

In recent years, the dairy industry has seen a drastic decrease in the reproductive efficiency of cows. This is reflected in undesirable decreases in such industry-standard reproductive performance measurements as (1) days to first service, (2) days to conception, (3) calving interval, (4) services per conception, (5) non-return rate, (6) estrus (or "heat") detection rate, and (7) pregnancy rate. Estrus, or heat, detection, in particular, is useful for identifying cows that are likely to become pregnant if inseminated at the time of estrus detection, or shortly thereafter. Wrongly identifying a cow as not being "in heat" (i.e., "estrus-negative") is a significant contributor to reproductive inefficiency. This has a corresponding significant impact on the dairy industry because dairy cows that are not reproductively efficient are culled.

SUMMARY

One aspect of the present invention is a method of selecting mammals receptive to embryo transfer, comprising: (1) synchronizing the estrous cycles of at least two mammals; (2) from the at least two mammals in step (1), selecting a mammal that has a corpus luteum (CL) present in its ovary; (3) transferring an embryo to the mammal selected in step (2); and (4) testing receptivity of the mammal towards pregnancy.

Thus, in one embodiment, the present invention provides a method for identifying a mammal receptive to embryo transfer, comprising (A) synchronizing the estrous cycles of two or more mammals; (B) transferring an embryo to a mammal that has a corpus luteum but has been identified as not in estrus or estrus-negative; and (C) testing the mammal for pregnancy, wherein a pregnant mammal indicates the mammal's receptivity to embryo transfer.

In one embodiment, the mammals are cows. In another embodiment, synchronizing is achieved by administering prostaglandin to the at least two mammals. In another embodiment, synchronizing is achieved by administering one or more of prostaglandin, gonadotropin and progestin.

In another embodiment, the mammals are cows and the presence of a corpus luteum is detected by a method selected from the group consisting of (i) rectal palpation; (ii) ultrasonography; (iii) measuring the concentration of progesterone in the blood of the cow; and (iv) measuring the concentration of the progesterone in the milk produced by the cow.

In another embodiment, the mammals are cows and the embryo is between 5 days and 10 days old.

In another embodiment, the mammals are "estrus-negative", i.e., the mammals are not "in heat or do not show outward signs of heat." In a further embodiment, the at least two estrus-negative mammals are cows.

In another embodiment, the synchronizing is achieved by administering prostaglandin to the at least two estrus-negative cows. The prostaglandin may be used in conjunction with other pharmaceuticals in a synchronization program.

In another embodiment, wherein the presence of a corpus luteum in the at least two estrus-negative cows is detected by a method selected from the group consisting of (i) rectal palpation; (ii) ultrasonography; (iii) measuring the concentration of progesterone in the blood of the cow; and (iv) measuring the concentration of the progesterone in the milk produced by the cow.

In a further embodiment, the embryo to be transferred to the at least two estrus-negative cows is between 5 days and 8 days old.

In a further embodiment, the embryos to be transferred are fresh embryos, frozen embryos, vitrified embryos, in vivo embryos, in vitro fertilized embryos, embryos produced by somatic cell nuclear transfer, embryos produced by embryonic cell nuclear transfer, embryos produced by embryonic splitting, embryos produced by sperm microinjection, embryos produced by genetic modification, and/or embryos produced by genetic selection.

In a further embodiment, the mammal to receive the embryo is in the estrous cycle between day 6 and day 10.

An additional embodiment comprises detecting whether the mammals are in estrus or "in heat", so as to identify estrus-positive and estrus-negative mammals.

An additional embodiment comprises detecting whether an ovarian corpus luteum is present in the mammals that have been identified as not in estrus or estrus-negative.

Another aspect of the invention is a method for selecting mammals receptive to embryo transfers, comprising: (1) synchronizing the estrous cycles of at least two mammals; (2) from the at least two mammals in step (1), selecting a mammal that is estrus-negative; (3) from the mammal in step (2), selecting a mammal that has a corpus luteum (CL) present in its ovary; (4) transferring an embryo to the mammal selected in step (3); and (5) testing receptivity of the mammal towards pregnancy.

In one embodiment, the method for selecting mammals receptive to embryo transfers further comprises between step (1) and (2) selecting an estrus-positive mammal from the at least two mammals, wherein an embryo is transferred to the estrus-positive mammal and the CL-bearing mammal selected in step (3) In another embodiment, the at least two mammals are cows.

In one embodiment, the method for selecting mammals receptive to embryo transfers further comprises between step (1) and (2) selecting an estrus-positive mammal from the at least two mammals, wherein an embryo is transferred to the estrus-positive mammal and the CL-bearing mammal selected in step (3) and wherein the milk production from the estrus-positive mammal and the CL-bearing mammal is at least 1% higher than the milk production from the estrus-positive mammal alone. In this regard, the milk production from the estrus-positive mammal and the CL-bearing mammal can be 1-5%, 5-10%, 10-15%, 15-20%, 20-25%, 25-30%, 30-35%, 35-40%, 40-45%, 45-50% higher than the milk production from the estrus-positive mammal alone.

In another embodiment, the estrus-positive cows are selected by a method selected from the group consisting of:

(i) tail marking; (ii) watching estrus signs; (iii) using marker animals; (iv) mounting-activity detectors; (v) measuring methyl heptanol and (vi) measuring pheromone (vii) measuring motion (viii) measuring temperature.

In another embodiment, the at least two mammals are cows and the synchronizing is achieved by administering prostaglandin to the at least two mammals. In another embodiment, the synchronizing is achieved by administering one or more of prostaglandin, gonadotropin and progestin to the cows.

In another embodiment, the at least two mammals are cows and the presence of a corpus luteum is detected by a method selected from the group consisting of: (i) rectal palpation; (ii) ultrasonography; (iii) measuring the concentration of progesterone in the blood of the cow; and (iv) measuring the concentration of the progesterone in the milk produced by the cow.

In yet another embodiment, the embryo to be transferred to the at least two cows is between 5 days and 10 days old. In yet another embodiment, the embryos to be transferred are fresh embryos, frozen embryos, vitrified embryos, in vivo embryos, in vitro fertilized embryos, embryos produced by somatic cell nuclear transfer, embryos produced by embryonic cell nuclear transfer, embryos produced by embryonic splitting, embryos produced by sperm microinjection, embryos produced by genetic modification, and/or embryos produced by genetic selection.

In yet a further embodiment, the cow to receive the embryo is in the estrous cycle between day 6 and day 10.

Another aspect of the invention is a kit to increase reproductive efficiency of mammals, comprising: (1) at least one estrus-detecting reagent or device, (2) at least one corpus luteum (CL)-detecting reagent or device, (3) at least one warming or thawing medium and (4) at least one transfer medium.

In one embodiment, the at least one estrus-detecting device is a mounting-activity detector or motion activity detector. In another embodiment, the at least one CL-detecting reagent comprises an antibody against progesterone and an antibody against the antibody against progesterone.

Another aspect of the invention is a kit to impregnate one or more estrus-negative cows, comprising: (1) at least one corpus luteum detecting reagent or device; and (2) at least one embryo to be transferred to at least one cow that has been identified to have a corpus luteum by said corpus luteum detecting reagent or device.

In one embodiment, wherein the corpus luteum detecting reagent comprises an antibody against progesterone and an antibody against the antibody against progesterone.

In another embodiment, the embryos to be transferred are fresh embryos, frozen embryos, vitrified embryos, in vivo embryos, in vitro fertilized embryos, embryos produced by somatic cell nuclear transfer, embryos produced by embryonic cell nuclear transfer, embryos produced by embryonic splitting, embryos produced by sperm microinjection, embryos produced by genetic modification, and/or embryos produced by genetic selection.

Another aspect of the invention is a method of increasing milk production, comprising: (1) synchronizing the estrous cycles of at least two mammals; (2) from the at least two mammals in step (1), selecting a mammal that is estrus-negative; (3) from the mammal in step (2), selecting a mammal that has a corpus luteum (CL) present in its ovary; (4) transferring an embryo to the mammal selected in step (3); and (5) testing receptivity of the mammal towards pregnancy.

In one embodiment, the method of increasing milk production further comprising synchronizing the estrus cycles of the cows.

In another embodiment, the synchronization is achieved by administering prostaglandin to the cows. In another embodiment, the synchronizing is achieved by administering one or more of prostaglandin, gonadotropin and progestin to the cows.

In another embodiment of the method of increasing milk production, the presence of a corpus luteum is detected by a method selected from the group consisting of: (i) rectal palpation; (ii) ultrasonography; (iii) measuring the concentration of progesterone in the blood of the cow; and (iv) measuring the concentration of the progesterone in the milk produced by the cow.

In yet another embodiment of the method of increasing milk production, the embryo is between 5 days and 10 days old. In yet another embodiment, the embryos to be transferred are fresh embryos, frozen embryos, vitrified embryos, in vivo embryos, in vitro fertilized embryos, embryos produced by somatic cell nuclear transfer, embryos produced by embryonic cell nuclear transfer, embryos produced by embryonic splitting, embryos produced by sperm microinjection, embryos produced by genetic modification, and/or embryos produced by genetic selection.

In yet a further embodiment, the cow to receive the embryo is in the estrous cycle between day 6 and day 10.

A further aspect of the invention is a method for improving the pregnancy rate of a cow population, comprising: transferring an embryo into a cow that has been identified as estrus-negative, and wherein the estrus-negative cow has been synchronized by administering one or more of prostaglandin, gonadotropin and progestin.

DETAILED DESCRIPTION

Maximizing the number of cows in a herd that can become pregnant—and therefore begin lactating to produce milk—is a chief goal among dairy farmers. In the dairy industry, monitoring the pregnancy rate of cows is a standard way to measure the reproductive performance of individual cows. And the parameter of pregnancy rate is calculated as the conception rate multiplied by estrus ("in heat") detection rate. In the estrus phase of the estrous cycle, females become sexually receptive and are often observed as "in heat." Each cow may experience seventeen estrous cycles per year if they do not become pregnant and they reside in locations where adequate light and nutrition is available year round. The estrous cycle generally consists of four phases: (1) proestrus; (2) estrus; (3) metestrus and (4) diestrus. The corpus luteum is a structure that often protrudes from the edge of the ovary and can be differentiated from the follicle by palpation or ultrasound. The ovarian follicle usually contains a single oocyte and is found at the cortex, or outer part, of the ovary. The corpus luteum, which derives from ovarian follicles, is also located at the ovarian cortex Developmentally, during each estrus phase, ovarian follicles develop into maturity under the influence of estrogen and gonadotropic hormones. For some mammals such as cows, spontaneous ovulation may occur in the estrus phase, while in other species, ovulation requires sexual intercourse.

With respect to cows, and the calculation of pregnancy rates, the heat detection rate is determined by the fraction of cows that are identified as being in estrus during a 21 day period, via various methods discussed in methods below. An important point is that variability in correct heat detection can have a dramatic effect on the pregnancy rate of the collective herd. For instance, if the conception rate is 40%, and the heat detection rate is identified as 50%, then the pregnancy rate would equal 20% (PR=0.4*0.5=0.2). However, if all cows were correctly identified as being in heat, or in estrus, then the pregnancy rate would double to 40% (PR=0.4*1.0=0.4). Consequently, misidentifying the numbers of cows that could actually become pregnant by artificial insemination or embryo transfer, but which were otherwise culled because "no heat" was detected, can significantly reduce the productivity of the entire herd. In addition, incorrect identification of estrus, and breeding cows that are not in estrus, costs the dairymen for the wasted semen and lost time while waiting to determine if the animal is pregnant. Therefore, breeding all animals synchronized is also costly.

The present invention maximizes the number of cows selected from a herd to be recipients for embryo transfer by identifying additional animals not seen in estrus "estrus-negative" that are still receptive to embryo transfer, and thus pregnancy. "Receptive" typically refers to the hormone-induced, thickened condition of the uterine lining that provides nourishment for the implanted embryo. The present invention allows dairy producers to impregnate cows that had not shown signs of estrus. Although these cows were capable of becoming pregnant they would not have been identified using other protocols. In addition, this new protocol also provides a superior method for impregnating cows over the standard timed artificial insemination method, because it can permit fewer shots and fewer drugs to be administered to cows over time.

Artificial insemination refers to the introduction of semen into the vagina or uterus by mechanical or instrumental means rather than by sexual intercourse. Artificial insemination is planned to coincide with the expected time of ovulation so that fertilization can occur. Timed artificial insemination protocols are designed to synchronize ovulation among a group of cows that are often in various stages of the estrous cycle at the initiation of the program. In short, the present invention provides an alternative and preferred method to increase pregnancies and therefore lifetime milk production.

The present invention identified that cows that were classified as estrus-negative, i.e., cows that were not identified as in heat, but which had a corpus luteum in the ovary, were in fact receptive to embryo transfer, and could become pregnant. Thus, the present inventive method permits the identification of reproductively sound cows from the subpopulation of cows in the herd that would otherwise have been culled. That is, normally, a dairy farmer will segregate and cull or first use other strategies such as timed AI to increase the number of pregnancies and then cull. Typically they would only use those identified as being in heat for embryo transfer or artificial insemination to become pregnant. Many reproductively sound cows, particularly on dairy's, do not show heat because of things like poor footing, negative energy balance, excessive heat and inadequate ventilation, inadequate space, inadequate bedding etc. and therefore have a silent or estrus-negative heat. By using the present inventive method, however, the dairy farmer can increase the reproductive efficiency of the cattle herd by recategorizing the to-be-culled subpopulation so as to identify estrus-negative cows that nonetheless are still able to become pregnant. Thus, any variability in heat detection can be corrected for by detecting the presence of corpus luteum in the estrus-negative cows, allowing more cows per herd to be used for reproduction, and thus milk production.

Accordingly, one aspect of the present inventive method is identifying the presence of a corpus luteum in estrus-negative cows. The present invention does not require an initial detection of estrus, or non-detection of estrus, as the case may be. Rather, the present invention also accommodates simply the detection of corpus luteum in all cows regardless of whether or not they have been subjected to estrus/heat detection. Furthermore, the present invention is not limited to use only in cows. Other female mammals can be subjected to the inventive test to determine whether they are suitably biologically, and receptive for reproductive activities. Thus, other animals, including horses, dogs, cats, sheep, goats, camelids, pachyderms, as well as others, can be tested for the presence of a corpus luteum, or identified as being in heat, or not in heat, and the latter subsequently tested for the presence of a corpus luteum prior to application of reproductive technology, such as by embryo transfer. Thus, citation to "cows" as used elsewhere herein is only an illustrative example, and not meant to be interpreted as limiting the inventive method to only that species of animal.

Thus, in one embodiment, a subpopulation of estrus-negative cows is provided that are nonetheless receptive to embryo transfer. This particular embodiment therefore concerns identifying those cows from a herd that are not seen in heat, and then testing those estrus-negative cows to determine which contain a corpus luteum (CL). These estrus-negative, CL-positive cows are then implanted with embryos, and, of that subpopulation, some will become pregnant. Accordingly, present invention combined with appropriate synchronization increases the reproductive efficiency of the herd.

In this regard, the corpus luteum is a temporary endocrine structure developed from an ovarian follicle during the metestrus and diestrus phases of the estrous cycle in mammals. The corpus luteum produces high levels of progesterone, which thicken and maintains the uterine lining in preparation for implantation of an embryo. In the absence of a viable embryo, the corpus luteum stops secreting progesterone and regresses into a scar tissue, while the uterine lining consequently degenerates back to normal size. With the presence of a viable embryo, however, the corpus luteum continues to secrete progesterone, which in turn maintains the thick uterine lining to provide the necessary nourishment for the development of the embryo.

There are three standard ways to detect the corpus luteum: (1) rectal palpation; (2) ultrasonography; and (3) measuring progesterone levels in the blood or milk produced by the mammal. In the case of rectal palpation in cows, the cervix is first typically detected by hand, touch and feel in order to identify the uterus, which is characterized by an external bifurcation between the two uterine horns. The next step is to detect the ovaries, which are typically located underneath or to the side of the uterus. The corpus luteum is a structure that often protrudes from the edge of the ovary and can be differentiated from the follicle by palpation or ultrasound. The ovarian follicle contains a single oocyte and is found at the cortex, or outer part, of the ovary. The corpus luteum, which derives from ovarian follicles, is also located at the ovarian cortex.

When performing ultrasonography, a probe is inserted through the rectum and positioned above the ovary. Pulses of ultrasound are generated by the probes and transmitted to the tissues adjacent to the probe. From the adjacent tissues, the pulses of ultrasound are reflected back to the probe. The amount of the reflection depends on the structure of the adjacent tissues. The corpus luteum is typically seen as a distinct grayish echogenic area within the ovarian stroma and could contain a cavity. Ultrasonography offers a highly reliable way of detecting corpus luteum, however, equipment is costly.

Lastly, the corpus luteum can be detected by measuring the concentration of the hormone progesterone in the cow's blood or milk. Assay kits are commercially available to determine progesterone level in blood or milk. For example, a "Target Equine Progesterone Kit" is available from Bio-Metallics Incorporated, Princeton, N.J., USA. A QUICK-CHECK™ Canine Progesterone Kit and a QUICK-CHECK™ Equine Progesterone Kit are available from Exodus Breeders Corporation in York, Pa., USA.

As mentioned above, the present inventive method permits the identification of cows containing a corpus luteum as suitable candidates for embryo transfer regardless of whether or not the cows have been classified as in heat or not in heat.

There are various traditional methods for determining whether a cow is in heat. Mammals in heat, i.e., that are in the estrus phase of the estrous cycle, usually display certain estrus signs. In the case of cows, these signs include: (1) standing to be mounted by another cow, which is the most commonly used sign in the industry for estrus detection; (2) greater physical activity as a result of increased nervousness and restlessness; (3) licking and sniffing of the genital areas of other cows; (4) bawl or bellow frequently; (5) a thin, clear, watery mucus discharge from vulva; and (6) reduced feed intake. Because many of these individual signs require human observation and even then can be subtle in nature, a determination of whether a cow or other mammal is in heat should be based on the totality of all signs. A mammal is deemed "estrus-positive" if it is determined that the totality of all signs points to estrus. Conversely, a mammal is deemed "estrus-negative" if it is determined that the totality of all signs does not point to estrus.

Specifically, whether a cow is in heat or not can be identified by "standing heat" and "tail chalk". Those in "standing heat" showed behavioral estrus by standing to be jumped by another cow. Further, "tail chalk" can be used to identify cows in estrus—by painting the tail head of all cows synchronized and observing whether the paint is rubbed off. If the paint is rubbed off, the cow is recorded as having shown sign of estrus.

The dairy farmer is aware of many of the practical ways in which the aforementioned signs can be detected. "Marker animals," for example, are surgically-altered bulls or androgenized cows or steers, that are sexually active and seek out cows in estrus. Androgenized cows are cows injected with testosterone and simulate male behavior. These marker animals are typically equipped with a marking device, such as a halter that works like a ball-point pen under the marker mammal's chin. When the marker bull mounts a cow that is in heat, the chin-ball marker leaves mark on the female mammal's back. These marks can then be interpreted to determine whether the female mammal is in heat. Similarly, mounting-activity detectors attached to a cow can change color upon sexual activity, while electronic detectors transmit radio signals to a computer that records the identity of the cow, and the time and duration of the mount. Electronic detectors are more accurate than other types of detectors because they can record multiple mounts and the duration of the mount. Alternatively, increased levels of methyl heptanol in a cow's vaginal secretions indicates it is in heat. Methyl heptanol can be monitored through gas chromatography as described, for instance, in U.S. Pat. No. 4,467,814, which is hereby incorporated by reference in its entirety. "Tail marking" is yet another method to detect estrus by placing chalk or paint in a band along a mammal's tailhead from hooks to pins. The chalk or paint is rubbed off by the mammal doing the mounting.

Accordingly, one of ordinary skill in the art would know how to detect cows that are in heat, or are not in heat, and subsequently identify in the latter (estrus-negative) subgroup, those cows which have a corpus luteum. The cows that are estrus-negative but CL-positive then can become candidate recipients of embryos in embryo transfer procedures.

In this regard, embryo transfer refers to various standard methods for establishing a pregnancy in which one or several embryos are isolated from at least one donor mammal and placed into the uterus of at least one other mammal. An in vivo embryo is one isolated from the donor mammal In addition to producing the embryo in a donor mammal, an embryo can also be produced with the process of in vitro fertilization (IVF). IVF refers to a process by which an egg is fertilized by a sperm outside the body. Embryos may be transferred fresh or after preservation by freezing or vitrifying in liquid nitrogen. Frozen/vitrified embryos are thawed/warmed prior to embryo transfer following protocols dependent on the preservation process and the tool used to contain the embryo. Frozen embryos can maintain their viability for long periods of time, likely because the low temperature effectively stops all biological activities, including biological reactions leading to apoptosis.

In one embodiment, the embryos to be transferred are produced in vitro by somatic cell nuclear transfer (i.e., cloning), which is exemplified in Kato et al., *Science* 282 (5396):2095-2098 (1998) and Wilmut et al., *Nature* 385: 810-813 (1997), both of which are hereby incorporated by reference in their entireties.

In another embodiment, the embryos to be transferred are produced in vitro by embryonic cell nuclear transfer, which is exemplified in Peura et al., *Mol. Reprod. Dev.* 50:185-191 (1998) and Smith et al., *Biology of Reproduction* 40(5): 1027-1035 (1989), both of which are hereby incorporated by reference in their entireties.

In a further embodiment, the embryos to be transferred are produced in vitro by embryo splitting or cleavage, which is exemplified in Gary et al., *Therigenology* 35(1):37-44 (1991) and Baker et al., *Therigenology* 23(1):3-12 (1985), both of which are hereby incorporated by reference in their entireties.

In an additional embodiment, the embryos to be transferred are produced in vitro by sperm microinjection, which is exemplified in Heuwieser et al., *Therigenology* 38(1):1-9 (1992), which is hereby incorporated by reference in its entirety. In one embodiment, the embryos to be transferred are produced in vitro by genetic modification, which is exemplified in Yang et al., *PLoS One* 6(3):e17593 (2011); Clark, *Am. J. Clin. Nutr.* 63:633-638 (1996); and Lai et al., *Reprod. Biol. Endocrinol.* 1:82 (2003), all of which are hereby incorporated by reference in their entireties.

In one embodiment, the embryos to be transferred are produced in vitro by genetic selection, which is exemplified in Bodo et al., *Acta Vet. Hung.* 49(1):99-109 (2001) and Chen et al., *Biology of Reproduction.* 67(5):1488-1492 (2002), both of which are hereby incorporated by reference in their entireties.

The embryo transfer procedure with respect to fresh or in vivo donor-generated embryos, generally comprises seven steps: (1) selection of donor mammal; (2) synchronization of donor mammal and recipient mammals; (3) superovulation of donor mammal (a process of manipulating the donor mammal to produce maximum number of eggs); (4) insemination of the donor (fertilization of donor eggs by sperm from selected males); (5) flushing the embryo (separating the embryos from the donor uterus); 65) evaluation of the embryo (classifying the embryos into different grades, such as excellent, good, fair, poor and dead); (7) selection of the recipient mammal (selecting female mammals that are receptive to embryo transfer); (8) transferring the embryos, which is a process of "loading" the embryo into a transfer gun, inserting the transfer gun through the cervix and then expelling the embryo in the forward tip of a uterine horn ipsilateral to the corpus luteum. In the case of in vitro produced embryo, only steps (5), (6) and (7) typically would apply. Sometimes it is desirable to select a donor mammal that is regarded to be "genetically superior" than other members of its species. Thus, in one embodiment of the present invention, embryo transfer can be used to increase the number of offsprings from genetically superior mammals. For instance, artificial insemination is a low cost alternative compared with maintaining bulls. Artificial insemination also provides the ability to select from a large number of bulls those that have particularly desirable traits. Embryo transfer has been used to maximize the reproductive potential of such elite cows that can be bred with those bulls. With the help of hormone stimulation, for example, elite cows can be subject to superovulation to produce 7-12 embryos per ovulation cycle to be transferred to other surrogate cows. At about 50% successful transfer rate, the number of calves from an elite cow therefore increases from one to more than six per ovulation cycle. Cows can be subject to superovulation multiple times in a year.

Various media used in embryo transfer are known in the art. For example, embryo flush can be used when removing in vivo embryos from a donor's uterus. Commercially available embryo flush include, for example, EmCare™ Complete Flush Media and Vigro™ Complete Flush Media from Reproduction Resources, as well as BoviPro™ Recovery Media from Minitube of America. Further, holding media can be used when manipulating embryos on a benchtop. Commercially available holding media include, for example, EmCare™ Holding Media, Vigro™ Holding Plus Media and Syngro Holding Media from Reproduction Resources, as well as BoviPro™ Holding Media from Minitube of America. Additionally, thawing media can be used for thawing frozen embryos. Commercially available thawing media include, for example, EmCare™ CSU Thawing Kit from Reproduction Resources, as well as BoviPro™ Rehydration Media from Minitube of America.

Before estrus detection and/or corpus luteum detection are performed, it can sometimes be desirable to "synchronize" a herd of cows to ensure substantially all members of the dairy herd are staged at the same or similar reproductive period of their respective estrous cycles. Synchronizing the estrous cycles generally means manipulating the reproductive process of a group of female mammals so that ovulation occurs at approximately the same time. Synchronized estrous cycles in cows, for instance, allow a breeder to schedule breeding activities for a group of cows during a predetermined period, thereby increasing the efficiency of artificial insemination, embryo transfer or other breeding techniques, useful for maximizing the reproductive efficiency of the entire herd.

Synchronization can be achieved through the application three primary groups of hormones: prostaglandins, progestins, and gonadotropins. There are commercial products available for each group of hormones. Prostaglandin products include Lutalyse, Estrumate, and IN-SYNCH. Progestin products include the vaginal implant CIDR® and the feed additive Melengestrol Acetate (MGA). Gonadotropins products include Cystrorelin, Factrel, and Fertagyl. Antibodies can be used to detect these hormones. As is well known, an antibody is a protein employed by the immune system to recognize and neutralize foreign objects such as bacteria and virus. The target of an antibody is termed an antigen. The antibody typically recognize a unique part ("epitope") of an antigen. In addition to bacteria and viruses, modern molecular biology techniques now allow a skilled artisan to raise antibodies against almost any protein and then use the antibody as an assay tool as well as diagnostic or therapeutic tool.

"Prostaglandin" is a group of 20-carbon fatty acid hormones, secreted by the uterine endometrium, which causes the regression of corpus luteum and thereby induces a sharp drop of progesterone produced by the corpus luteum. With the removal of progesterone, gonadotropin-releasing hormone (GnRH) starts to exert greater influence. The higher level of GnRH leads to higher level of follicle-stimulating hormone (FSH) and luteinizing hormone (LH), which supports follicular development as the mammal enters the proestrus phase of the estrous cycle. "Progesterone" is a 21-carbon hormone that works through the intracellular progesterone receptor to exert a number of physiological effects, including (1) converting the endometrium, or uterine lining, to its secretory stage to prepare for the implantation of fertilized egg; (2) decreasing maternal immunity during implantation for the female mammal's body to accept pregnancy without an immune reaction; (3) decreasing the contractibility of the uterine smooth muscle; and (4) inhibiting lactation during pregnancy. During the metestrus phase of the estrous cycle, the newly formed corpus luteum starts to secret low level of progesterone. The corpus luteum then secretes high levels of progesterone during the diestrus phase.

A number of protocols can be employed to achieve synchronization, such as administering one hormone or a combination of hormones. For instance, prostaglandin may be injected individually in one of the four ways:

(1) A single injection of prostaglandin is administered and estrus is detected in the following 2-5 days.

(2) Estrus is detected in the first five days, and all female mammals found to be in heat were bred. Then a single injection of prostaglandin is administered on the fifth day to the female mammals that were not in heat.

(3) A first injection of prostaglandin is administered and estrus is detected in the next 5 days. On the $11^{th}$ day, a second injection of prostaglandin is administered to the female mammals that were not in heat.

(4) A first injection of prostaglandin is administered and estrus is detected in the next 5 days. On the 14$^{th}$ day, a second injection of prostaglandin is administered to the female mammals that were not in heat.

The administration of multiple shots of prostaglandins is typically referred to by a person skilled in the art as the two-shot method. See DuPonte M W and Lee K K, Three Simplified Estrus Synchronization Programs for Hawaii's Beef Breeding Season, *Livestock Management* (Cooperative Extension Service, University of Hawaii at Manoa), April 2007, LM-14, 1-2, which is hereby incorporated by reference in its entirety.

Prostaglandin can also be administered together with a progesterone-like feed additive Melengestrol Acetate (MGA). MGA can be fed for 14 days and then withdrawn. A single injection of prostaglandin then is administered 17 to 19 days after the MGA withdrawal.

In one embodiment, after synchronizing the cows with a single injection of prostaglandin, no other synchronizing agent is administered to the cows before the detection of corpus luteum. In another embodiment, after synchronizing the cows with a single injection of prostaglandin, no other synchronizing agent is administered to the cows before embryo transfer.

Synchronization can also be achieved through the combination of prostaglandin and vaginal implant CIDR®. Typically the CIDR implant is inserted on Day 0, one injection of prostaglandin is given on Day 6, and the CIDR implant is removed on Day 7. Estrus can be detected from Day 8 to Day 11. Further examples of synchronization methods include the combination of gonadotropins and prostaglandin. In the so-called "Select Synch protocol" (See Lamb G C, et al, Effectiveness of Select Synch (Gonadotropin-Releasing Hormone and Prostaglandin F2α) for Synchronizing Estrus in Replacement Beef Heifers, *The Professional Animal Scientist*, 20:27-33 (2004), incorporated by reference in its entirety), an injection of gonadotropin is administered on Day 0 with an injection of prostaglandin administered on Day 7. Estrus typically occurs 36 hour before and up to 6 days after the prostaglandin injection. The "Select Synch protocol" can be further modified to include a further gonadotropin injection 2 days after the prostaglandin injection.

Accordingly, one embodiment of the present methodology entails synchronizing a number of cows, detecting estrus in the synchronized cow population, and then detecting the presence of a corpus luteum in cows that are estrus-negative.

By increasing the numbers of cows identified as receptive to embryo transfer and subsequent pregnancy, the present invention also increases the number of lactating cows that correspondingly increases the quantity of milk that can be produced per unit time. Dairy cattle such as Holstein have been repeatedly and selectively bred for increased milk production, and such cows can be used in the context of the present inventive technology. While milk production level varies from breed to breed, one cow can typically produce around 15,000 to 25,000 lbs of milk per lactation period. Ten or more lactations are possible during a cow's lifetime. But most cows are culled after two lactations, mainly for four reasons: (1) infertility; (2) persistent and potentially fatal mammary gland infection; (3) persistent foot infection or leg problems causing infertility and loss of production; and (4) failure to produce economic levels of milk to justify their feed costs. The present invention therefore addresses the number one reason for culling dairy cows and maximizes the efficiency of the rate of pregnancy by identifying additional cows receptive to embryo transfer, and also maximizes the efficiency of milk production.

Figure 1:
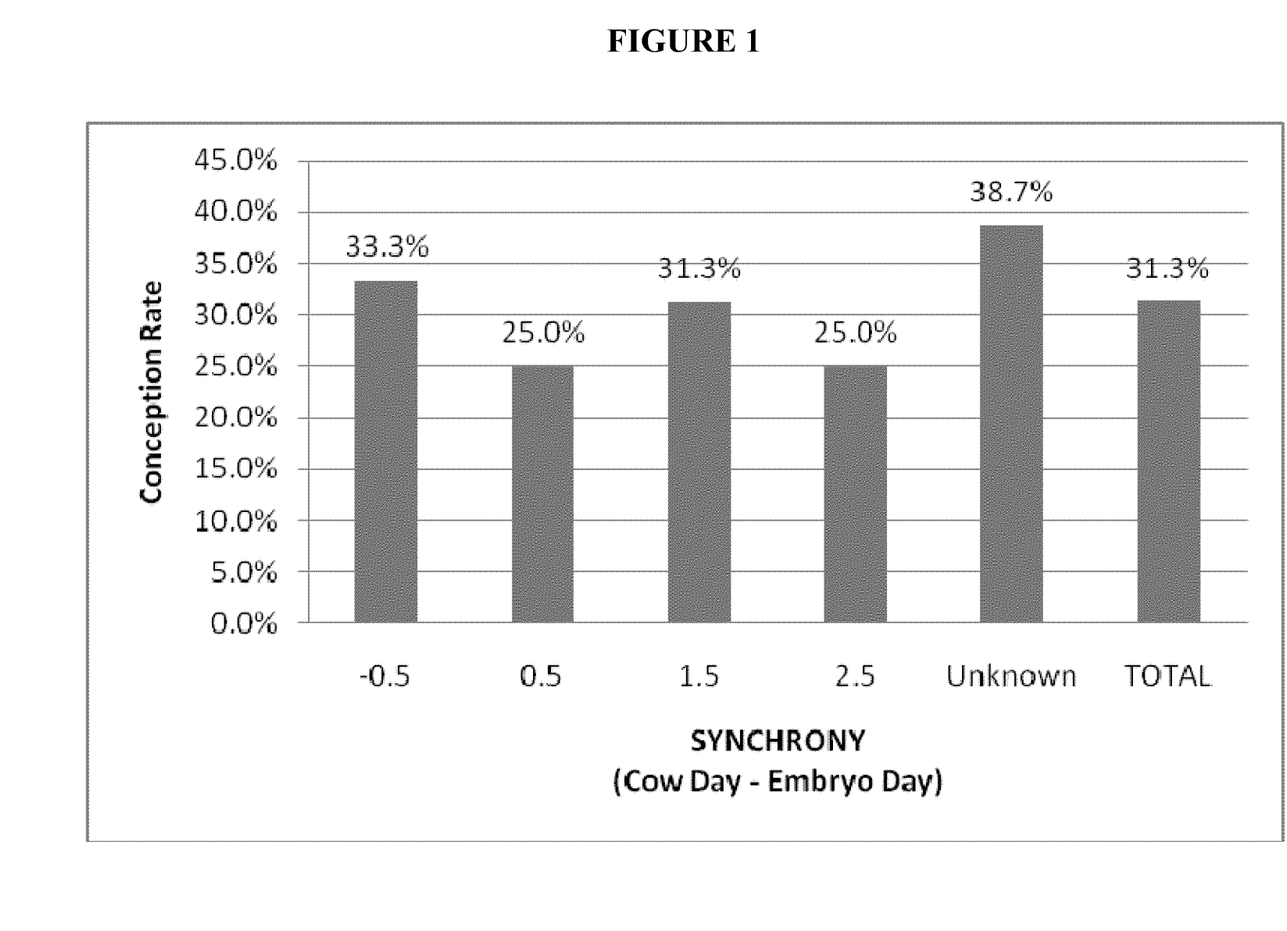
FIG. 1: Conception rates for animals in each synchrony group (not different to one another). (P>0.1).
Figure 2:
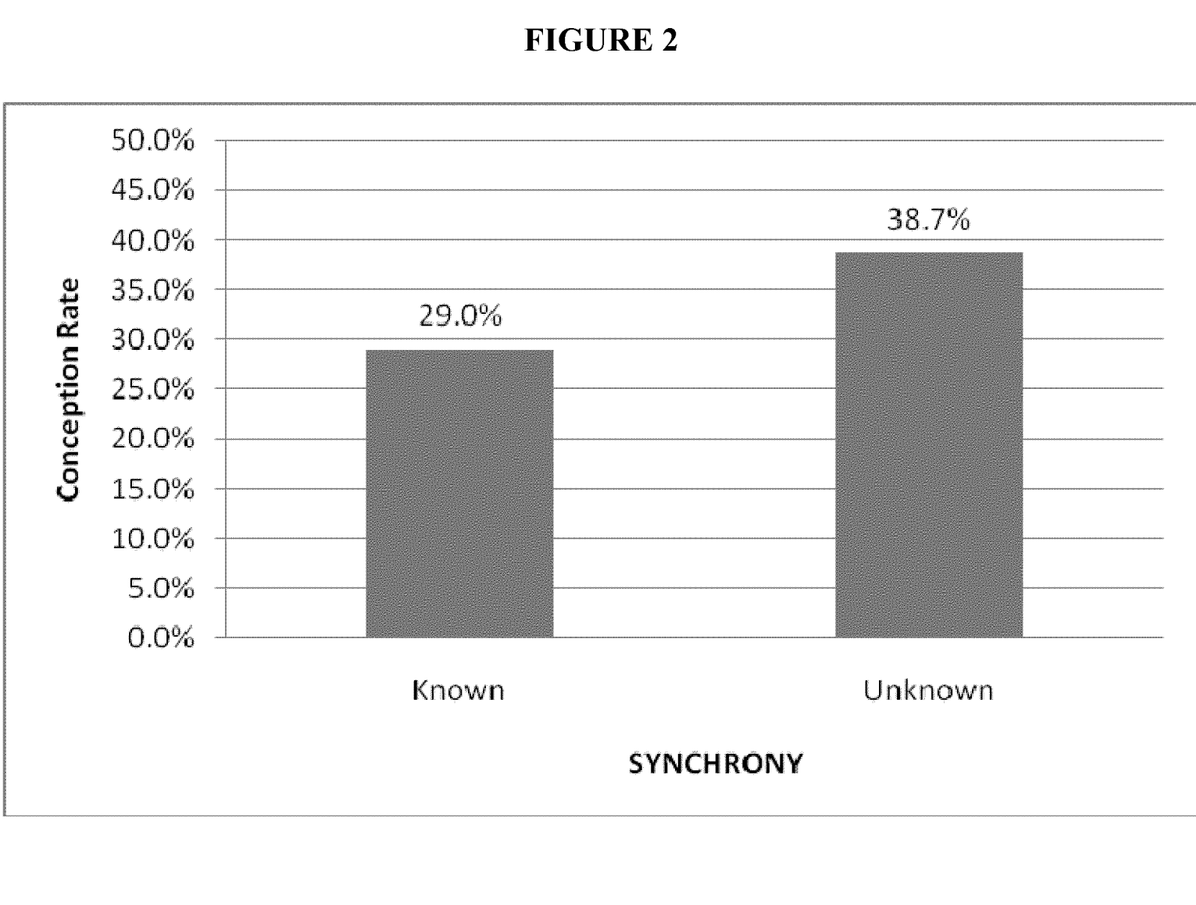
FIG. 2: Conception rates for animals in known and unknown synchrony groups were found not to be different. (P>0.1)

It was shown as disclosed elsewhere herein, that estrus was synchronized using a single intramuscular injection of Lutalyse injectable prostaglandin into cows, and estrus detected by observing tail chalk once daily. Fresh in vitro produced (IVP) embryos at Day 6.5 and 7.5, were then transferred to cows observed to be in estrus 11 days after Lutalyse injection on cow estrous cycle Days 6-10. Those cows that did not show signs of estrus were then subsequently palpated for a corpus luteum (CL). If a CL was detected an IVP embryo was transferred. Pregnancy was detected by palpation at approximately 40 days. Significantly, the cows which did not show estrus but did have a corpus luteum, had a conception rate of 38.7% (FIG. 1 and Table 1).

Similarly, in the same study disclosed herein, thirty-one additional cows were identified through CL palpation for embryo transfer which increased the total number of embryos transferred by 26%. This study shows that these cows, which would have remained undetected, were capable of becoming pregnant with an IVP embryo.

Furthermore, embryos have the unique ability to speed up or delay development in order to fit the stage of the uterine environment. Therefore the embryo and the uterus do not need to be in exact synchrony for a pregnancy to occur. This cannot be said for artificial insemination (AI). When AI occurs, it must be done within a very short time period (12 hour window). There are some protocols for timing AI so heat detection is unnecessary. However, these protocols require giving numerous injections and can take several weeks from beginning of the protocol to AI. If the service is unsuccessful repeating the protocol again takes many additional weeks.

Because the corpus luteum structure does not exist on the ovary until day 4-5 of the estrous cycle, 4-5 days after the necessary time for artificial insemination, the process of palpating a corpus luteum structure after synchronization is not applicable for artificial insemination programs. However, corpus luteum palpation is effective in embryo transfer, as the embryo is transferred on days 6-10 of the estrous cycle. The results from this study, for instance, as explained in detail in the Examples, showed that the conception rates of cows which did not show signs of estrus but had a corpus luteum, and in which an embryo was transferred, were not different than cows that were observed in estrus and known to be synchronized.

Thus, this new protocol will save dairy producers money in synchronization costs, as well as increasing the efficiency of obtaining pregnant animals, such as cows, that had not shown signs of estrus. Although these animals were capable of becoming pregnant they would not have been identified using current, existing protocols.

Unless defined otherwise, all technical and scientific terms used herein have the same meaning as commonly understood by one of ordinary skill in the art to which this invention belongs. Generally, the nomenclature used herein, and the laboratory procedures described herein, are those well known and commonly employed in the art. Standard techniques are used for mammal breeding and maintenance, analytical chemistry, molecular biology, enzymatic assays and pharmaceutical formulation and delivery. Generally, enzymatic reactions and purification and/or isolation steps are performed according to the manufacturers' specifications.

The following examples serve to illustrate various embodiments of the present invention and should not be construed, in any way, to limit the scope of the invention.

All references cited herein, including patents, patent application and publications, are hereby incorporated by reference in their entireties, where previously specifically incorporated or not.

Having now fully described this invention, it will be appreciated by those skilled in the art that the same can be performed within a wide range of equivalent parameters, concentrations and conditions, without undue experimentation. This application is intended to cover any variations, uses, or adaptations of the invention, following in general the principles of the invention, that include such departures from the present disclosure as come within known or customary practice within the art to which the invention pertains and as may be applied to the essential features hereinbefore set forth.

EXAMPLES

Example 1

Between July 2010 and January 2011 one hundred forty-eight Holstein, Holstein crossbred and Jersey cows were identified as repeat breeders by being over 120 days in milk or having had over 4 unsuccessful artificial insemination services. Estrus was synchronized using a single intramuscular injection of Lutalyse injectable prostaglandin (25 mg, Pfizer, New York, N.Y.). Estrus was detected by observing tail chalk once daily. Fresh in vitro produced (IVP) embryos, Day 6.5 and 7.5, were transferred to cows observed in estrus 11 days after Lutalyse injection on cow estrous cycle Days 6-10. Those cows that did not show signs of estrus were palpated for a corpus luteum (CL). If a CL was detected an IVP embryo was transferred. Pregnancy was detected by palpation at approximately 40 days.

Synchrony of cows and embryos were calculated as cow day minus embryo day and ranged from −0.5 to 2.5 Days. The highest proportions of animals were 0.5 and 1.5 Days. (n=85). Thirty-one animals that received embryos but did not show signs of estrus had an unknown synchrony. The overall Day 40 conception rate was 31.3% for animals in this study. Those cows with unknown synchrony, which did not show estrus but did have a CL, had a conception rate of 38.7% (FIG. 1 and Table 1).

In this study, dairy cattle were synchronized with one shot of Lutalyse. Lutalyse (prostaglandin) is able to cause regression of the corpus luteum (CL) on days 5 through 17 of the estrous cycle when a fully functional CL is present on the ovary. Luteolysis is the regression of the CL which allows onset of estrus. Those animals past day 17 of the cycle would have natural CL regression if a pregnancy had not been established. Only those animals between days 0 and 5 would not be synchronized. Therefore, on average the percentage of animals that would be synchronized for estrus within the next 5 days would be 76.2%. Many of these animals, however, would not show or may not be seen in heat. In this study tail chalk was used to detect estrus by once daily observation. The animals that were not detected were palpated for a CL. If a CL was present an embryo was transferred. Thirty-one additional animals were identified for embryo transfer which increased the total number of embryos transferred by 26%. This study shows that those undetected animals were capable of becoming pregnant with an IVP embryo.

Embryos have the unique ability to speed up or delay development in order to fit the stage of the uterine environment. Therefore the embryo and the uterus do not need to be in exact synchrony for a pregnancy to occur. This cannot be said for artificial insemination (AI). When AI occurs it must be done within a very short time period (12 hour window). There are some protocols for timing AI so heat detection is unnecessary. However, these protocols require giving numerous injections and can take several weeks from beginning of the protocol to AI. If the service is unsuccessful repeating the protocol again takes many weeks.

Because the CL structure does not exist on the ovary until day 4-5 of the estrous cycle, 4-5 days after the necessary time for artificial insemination, the process of palpating a CL structure on the ovary post synchronization is not applicable to AI programs. However, CL palpation is effective in embryo transfer, as the embryo is transferred on days 6-10 of the estrous cycle. Results from this study showed that the conception rates of animals which did not show signs of estrus but had a CL, and in which an embryo was transferred, were not different than animals that were observed in estrus and known to be synchronized. This new protocol saves dairy producers money in synchronization costs, as well as impregnating animals that had not shown signs of estrus. Although these animals were capable of becoming pregnant they would not have been identified using other protocols. In addition, this new protocol also provides a superior method for impregnating animals over the standard timed artificial insemination method, because it permits fewer shots and fewer drugs to be administered to animals over time. This protocol provides an alternative and preferred method to increase pregnancies and therefore lifetime milk production.

Synchrony of cows and embryos were calculated as cow day minus embryo day and ranged from −0.5 to 2.5 Days. The highest proportions of animals were 0.5 and 1.5 Days. (n=85). Thirty-one animals that received embryos but did not show estrus had an unknown synchrony. The overall Day 40 conception rate was 31.3%. Those cows with unknown synchrony, which did not show estrus but did have a CL, had a conception rate of 38.7% (FIG. 1) and Table 1 (no. of animals in each group and the % of those that conceived, P>0.1).

TABLE 1

| Synchrony | Pregnant | Open | Total | Conception Rate |
|---|---|---|---|---|
| −0.5 | 4 | 8 | 12 | 33.3% |
| 0.5 | 9 | 27 | 36 | 25.0% |
| 1.5 | 15 | 33 | 48 | 31.3% |
| 2.5 | 1 | 3 | 4 | 25.0% |
| Unknown | 12 | 19 | 31 | 38.7% |
| Total | 41 | 90 | 131 | 31.3% |

Example 2

Figure 3:
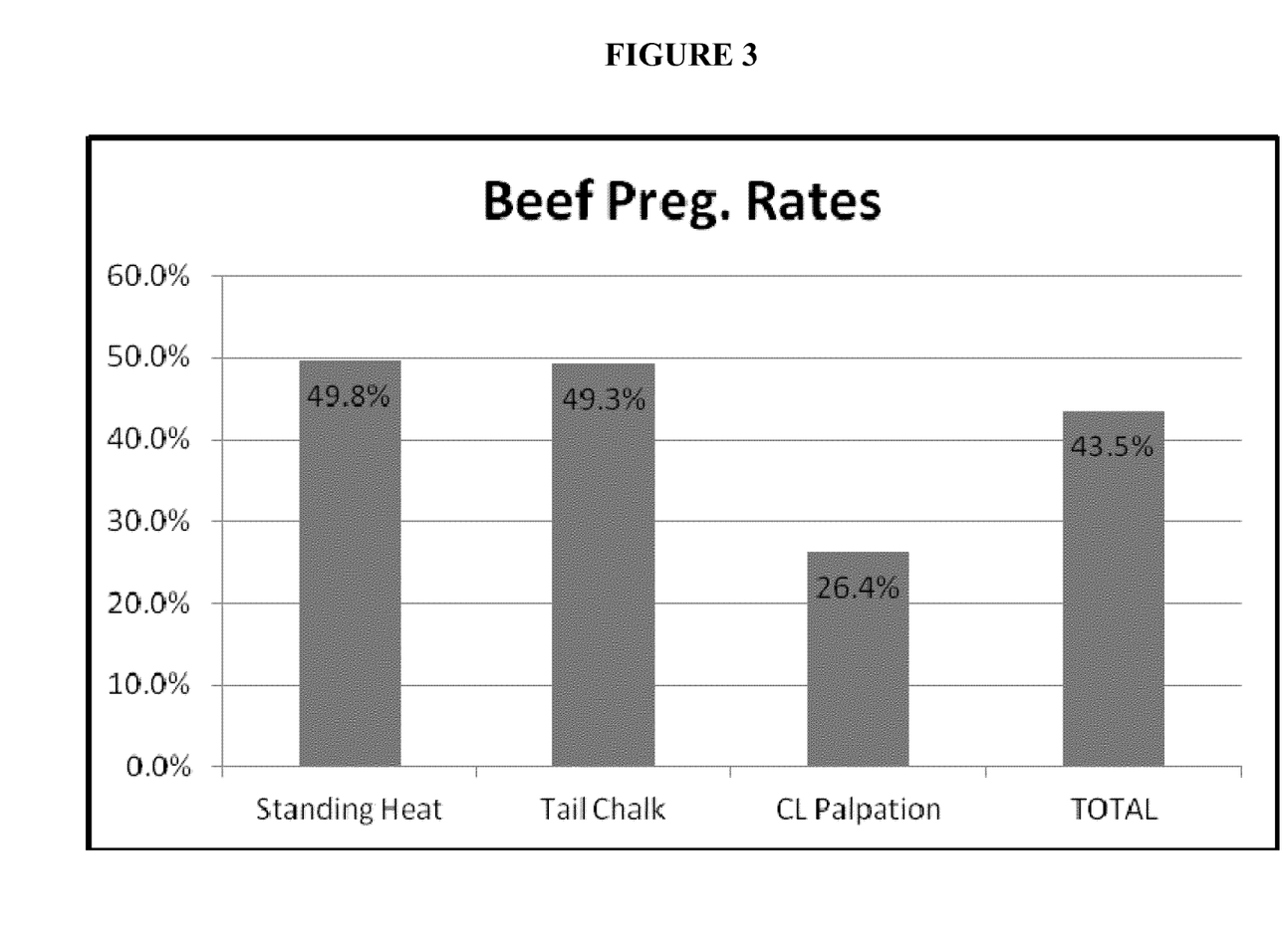
FIG. 3: Pregnancy rates for beef cows, including estrus-positive cows as identified by "standing heat", estrus-positive cows as identified by "tail chalk", and estrus-negative but CL-positive cows as identified by CL palpation.

FIG. 3 and Table 2 show the results from 490 IVF embryo transfers to older beef recipients from January 2011 to present. Animals were given one shot of Lutalyse and observed for signs of estrus. Those in standing heat showed behavioral estrus by standing to be jumped by another animal. Another method used to identify animals in estrus is by painting the tail head of all cows synchronized. If the paint is rubbed off the animal is recorded as having showed sign of estrus. By palpating for the presence or absence of a corpus luteum (CL) we were also able to infer that estrus had occurred when the CL is present. In vitro produced (IVP) embryos, Days 6.5, 7, 7.5 and 8, were transferred to both estrus-positive cows (cows observed in heat or showing outward signs of heat), and estrus-negative but CL-positive cows (cows not observed in heat or does not show outward signs of heat, but has CL present) 10 to 12 days after Lutalyse injection on cow estrous cycle Days 6-10. Due to our synchronization efforts, the estrus is assumed to have occurred in the time frame necessary for embryo transfer. Using CL palpation we were able to identify 129 additional animals for embryo transfer. Of those, 34 were confirmed pregnant at 30 days of gestation (26.4%). However, none of these animals would have had the opportunity to become pregnant. The drop in pregnancy rate is expected as the synchrony of the animals uterus and the embryo are unknown, but the fact that pregnancies do occur is significant.

TABLE 2

| Estrus Detection | PREG | OPEN | TOTAL | PREG RATE | OPEN RATE |
|---|---|---|---|---|---|
| Standing Heat | 106 | 107 | 213 | 49.8% | 50.2% |
| Tail Chalk | 73 | 75 | 148 | 49.3% | 50.7% |
| CL Palpation | 34 | 95 | 129 | 26.4% | 73.6% |
| TOTAL | 213 | 277 | 490 | 43.5% | 56.5% |

Example 3

Figure 4:
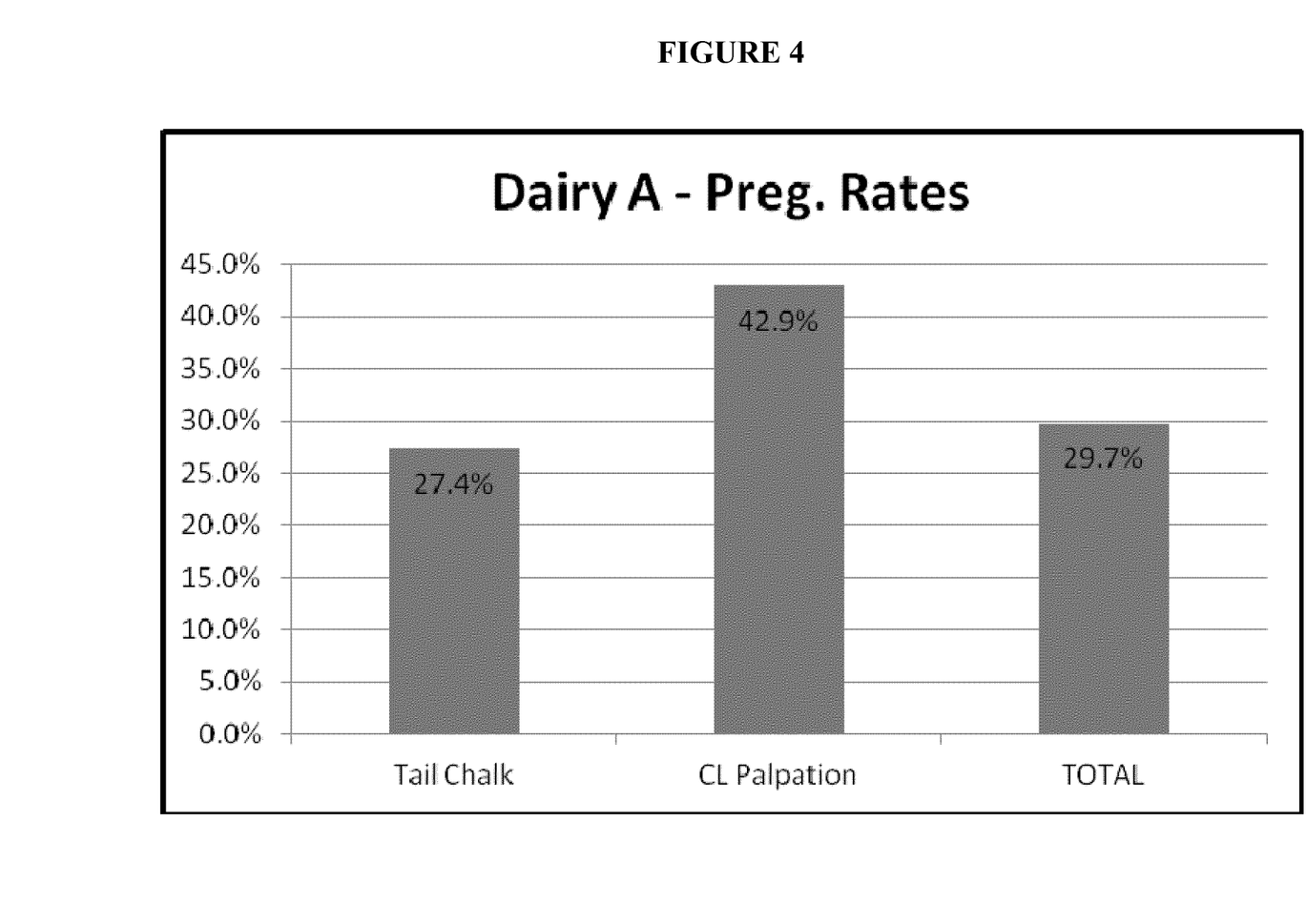
FIG. 4: Pregnancy rates for repeated breeder cows from Dairy A, including estrus-positive cows as identified by "tail chalk", and estrus-negative but CL-positive cows as identified by CL palpation.

FIG. 4 and Table 3 shows the results from 138 IVF embryo transferred at a working dairy (Dairy A) to repeat breeder animals from July to December 2010. Animals were given one shot of Lutalyse and observed for signs of estrus by looking for the absence of tail chalk. Twenty-one additional animals were identified for embryo transfer by using CL palpation. Of those, nine were confirmed pregnant at 45 days of gestation (42.9%). The 21 animals in the CL palpation group had not shown signs of estrus as the tail chalk had not been rubbed off the tail head. These animals would not have had the opportunity to become pregnant without the use of CL palpation and embryo transfer. Fresh in vitro produced (IVP) embryos, Day 6.5 and 7.5, were transferred to both estrus-positive cows (cows observed in heat or showing outward signs of heat), and estrus-negative but CL-positive cows (cows not observed in heat or does not show outward signs of heat, but has CL present) 11 days after Lutalyse injection on cow estrous cycle Days 6-10

TABLE 3

| Estrus Detection | PREG | OPEN | TOTAL | PREG RATE | OPEN RATE |
|---|---|---|---|---|---|
| Tail Chalk | 32 | 85 | 117 | 27.4% | 72.6% |
| CL Palpation | 9 | 12 | 21 | 42.9% | 57.1% |
| TOTAL | 41 | 97 | 138 | 29.7% | 70.3% |

Example 4

Figure 5:
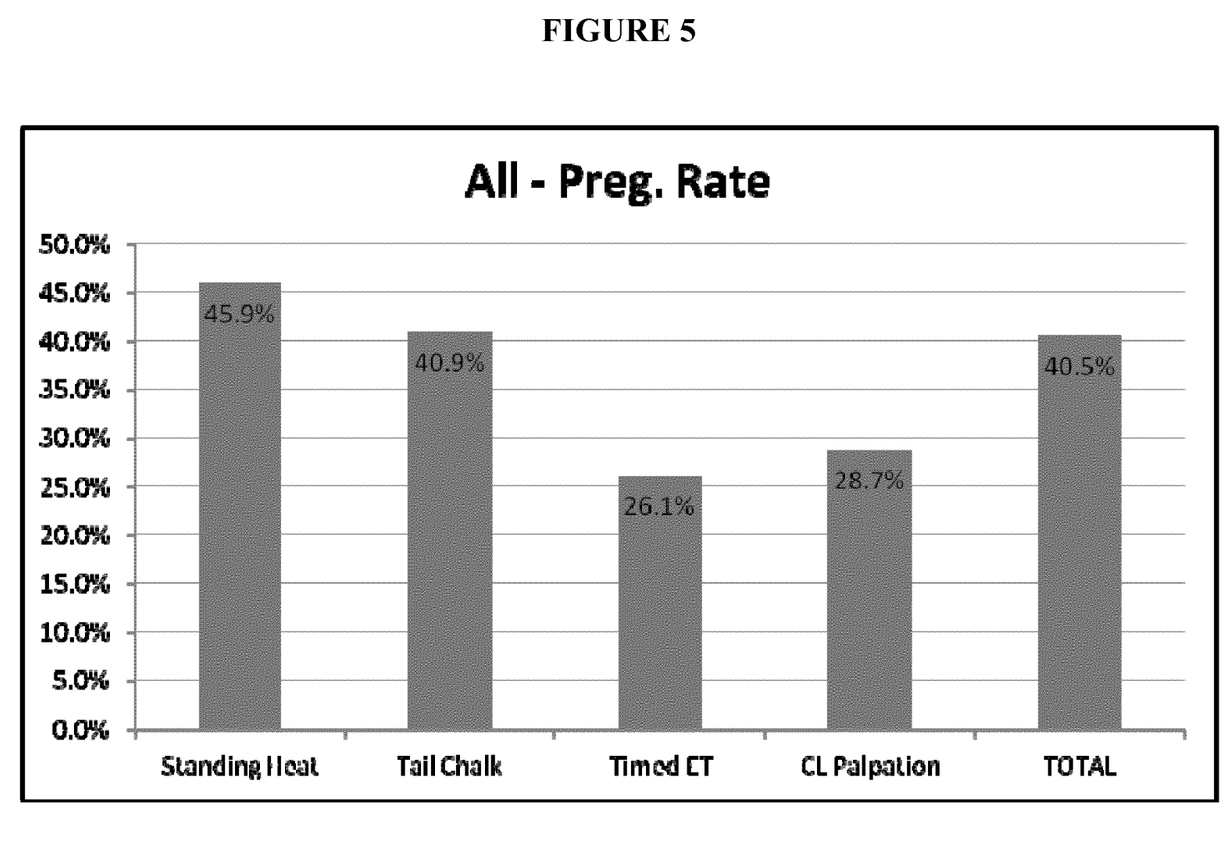
FIG. 5: Pregnancy rates for estrus-positive cows as identified by "standing heat", estrus-positive cows as identified by "tail chalk", estrus-negative but CL-positive cows as identified by CL palpation, and cows subjected to timed embryo transfer.

FIG. 5 shows results of 861 IVF embryo transfers to beef and dairy cattle from January 2010 to present. Using CL palpation we were able to identify a significant number of estrus-negative cows for embryo transfer. Of those, 28.7% were confirmed pregnant at 30-45 days of gestation. None of these animals would have had the opportunity to become pregnant if the embryos are only transferred to cows that were identified as "in heat", or estrus-positive.

What is claimed is:

1. A method for improving the pregnancy rate of a cow population via an embryo transfer procedure, comprising:
    a) synchronizing estrous cycles of a population of cows;
    b) performing an estrus detection procedure upon said population of cows from step a) and identifying a subpopulation of cows, which are not in heat or do not show outward signs of heat, from said population of cows from step a) by performing the estrus detection procedure;
    c) testing one or more cows from said subpopulation of cows from step b), which are not in heat or do not show outward signs of heat, for the presence or absence of a corpus luteum;
    d) identifying a cow from step c) that has a corpus luteum based upon said testing; and
    e) transferring an embryo to the cow identified as having the corpus luteum in step d) and testing said cow for pregnancy,
    wherein an improved pregnancy rate of the cow population is achieved.

2. The method of claim 1, wherein synchronizing estrous cycles in step a) is achieved by administering prostaglandin to the cows in step a).

3. The method of claim 1, wherein the presence of the corpus luteum in a cow that is not in heat or does not show outward signs of heat is detected in step c) by: (i) rectal palpation; (ii) ultrasonography; (iii) measuring the concentration of progesterone in the blood of the cow; or (iv) measuring the concentration of the progesterone in the milk produced by the cow.

4. The method of claim 1, wherein the embryo is between 5 days and 8 days old.

5. The method of claim 1, wherein the embryo is selected from the group consisting of: fresh embryos, frozen embryos, in vivo embryos, in vitro fertilized embryos, embryos produced by somatic cell nuclear transfer, embryos produced by embryonic cell nuclear transfer, embryos produced by embryonic splitting, embryos produced by sperm microinjection, embryos produced by genetic modification, and embryos produced by genetic selection.

6. The method of claim 1, wherein the embryo is transferred in step e) to said cow of said subpopulation that is not in heat or does not show outward signs of heat between day 6 and day 10 of the cow's estrous cycle.

7. The method of claim 1, wherein synchronizing estrous cycles in step a) is achieved by administering one or more of prostaglandin, gonadotropin, or progestin to the cows in step a).

8. The method of claim 1, wherein the presence of the corpus luteum in a cow that is not in heat or does not show outward signs of heat is detected in step c) by rectal palpation.

9. A method of decreasing the number of cows culled from a herd of cows, by selecting a subpopulation of cows from the herd that are receptive to embryo transfer, but would otherwise be culled from said herd as not being in heat or not showing outward signs of heat, the method comprising:
    a) synchronizing estrous cycles of cows in a herd;
    b) performing an estrus detection procedure upon said cows from step a) and identifying a subpopulation of cows from the herd, which are not in heat or do not show outward signs of heat by performing the estrus detection procedure;

c) testing one or more cows from said subpopulation of cows from step b), which are not in heat or do not show outward signs of heat, for the presence or absence of a corpus luteum;

d) identifying a cow from step c) that has a corpus luteum based upon said testing; and e) transferring an embryo to the cow identified as having the corpus luteum in step d), wherein a cow that subsequently becomes pregnant after embryo transfer is one that is receptive to embryo transfer, but otherwise would have been culled from the herd as not being in heat or not showing outward signs of heat.

10. The method of claim 9, wherein synchronizing estrous cycles in step a) is achieved by administering prostaglandin to the cows in step a).

11. The method of claim 9, wherein the presence of a corpus luteum in a cow that is not in heat or does not show outward signs of heat is detected in step c) by: (i) rectal palpation; (ii) ultrasonography; (iii) measuring the concentration of progesterone in the blood of the cow; or (iv) measuring the concentration of the progesterone in the milk produced by the cow.

12. The method of claim 9, wherein the embryo is between 5 days and 8 days old.

13. The method of claim 9, wherein the embryo is selected from the group consisting of: fresh embryos, frozen embryos, in vivo embryos, in vitro fertilized embryos, embryos produced by somatic cell nuclear transfer, embryos produced by embryonic cell nuclear transfer, embryos produced by embryonic splitting, embryos produced by sperm microinjection, embryos produced by genetic modification, and embryos produced by genetic selection.

14. The method of claim 9, wherein the embryo is transferred in step e) to said cow that is not in heat or does not show outward signs of heat between day 6 and day 10 of the cow's estrous cycle.

15. The method of claim 9, wherein synchronizing estrous cycles in step a) is achieved by administering one or more of prostaglandin, gonadotropin, or progestin to the cows in step a).

16. The method of claim 9, wherein the presence of the corpus luteum in a cow that is not in heat or does not show outward signs of heat is detected in step c) by rectal palpation.

17. A method of maximizing the number of cows selected from a herd to be recipients for embryo transfer, by identifying a subpopulation of cows from the herd that are not in heat or do not show outward signs of heat, but which are still receptive to embryo transfer, comprising:

a) synchronizing estrous cycles of cows in a herd;

b) performing an estrus detection procedure upon said cows from step a) and identifying a subpopulation of cows from the herd, which are not in heat or do not show outward signs of heat by performing the estrus detection procedure;

c) testing one or more cows from said subpopulation of cows from step b), which are not in heat or do not show outward signs of heat, for the presence or absence of a corpus luteum;

d) identifying a cow from step c) that has a corpus luteum based upon said testing; and e) transferring an embryo to the cow identified as having the corpus luteum in step d), wherein the embryo recipient cow would not otherwise have been given an embryo.

18. The method of claim 17, wherein the embryo is selected from the group consisting of: fresh embryos, frozen embryos, in vivo embryos, in vitro fertilized embryos, embryos produced by somatic cell nuclear transfer, embryos produced by embryonic cell nuclear transfer, embryos produced by embryonic splitting, embryos produced by sperm microinjection, embryos produced by genetic modification, and embryos produced by genetic selection.

19. The method of claim 17, wherein synchronizing estrous cycles in step a) is achieved by administering one or more of prostaglandin, gonadotropin, or progestin to the cows in step a).

20. The method of claim 17, wherein synchronizing estrous cycles step a) is achieved by administering prostaglandin to the cows in step a).

21. The method of claim 17, wherein the presence of a corpus luteum in a cow that is not in heat or does not show outward signs of heat is detected in step c) by rectal palpation; (ii) ultrasonography; (iii) measuring the concentration of progesterone in the blood of the cow; or (iv) measuring the concentration of the progesterone in the milk produced by the cow.

22. The method of claim 17, wherein the presence of the corpus luteum in a cow that is not in heat or does not show outward signs of heat is detected in step c) by rectal palpation.

23. The method of claim 17, wherein the embryo is between 5 days and 8 days old.

24. The method of claim 17, wherein the embryo is transferred in step e) to said cow that is not in heat or does not show outward signs of heat between day 6 and day 10 of the cow's estrous cycle.

* * * * *